United States Patent
Porter et al.

(10) Patent No.: US 9,149,550 B2
(45) Date of Patent: Oct. 6, 2015

(54) AIR AND FABRIC FRESHENER

(71) Applicant: Innovasouce, LLC, Huntersville, NC (US)

(72) Inventors: Sandra N. Porter, Huntersville, NC (US); Glenn F. Cueman, Denver, NC (US)

(73) Assignee: Innovasource, LLC, Huntersville, NC (US)

( * ) Notice: Subject to any disclaimer, the term of this patent is extended or adjusted under 35 U.S.C. 154(b) by 0 days.

(21) Appl. No.: 13/633,581

(22) Filed: Oct. 2, 2012

(65) Prior Publication Data
US 2014/0093471 A1   Apr. 3, 2014

(51) Int. Cl.
*A61L 9/01* (2006.01)

(52) U.S. Cl.
CPC ........................................ *A61L 9/01* (2013.01)

(58) Field of Classification Search
None
See application file for complete search history.

(56) References Cited

U.S. PATENT DOCUMENTS

| | | | |
|---|---|---|---|
| 3,102,101 A | 8/1963 | Hawley et al. | |
| 4,238,192 A | 12/1980 | Kandathil | |
| 5,104,644 A * | 4/1992 | Douglas | 424/53 |
| 5,942,153 A | 8/1999 | Heydel | |
| 6,383,523 B1 * | 5/2002 | Murad | 424/616 |
| 6,495,097 B1 | 12/2002 | Streit et al. | |
| 2006/0280665 A1 | 12/2006 | Rees et al. | |
| 2009/0226389 A1 | 9/2009 | Warr et al. | |
| 2010/0113808 A1 * | 5/2010 | Liebens et al. | 549/531 |

OTHER PUBLICATIONS

SciFinder, SciFinder—Anachidonic Acid, "Risk of Colorectal Cancer Is Linked to Erythrocyte Compositions of Fatty Acids as Biomarkers for Dietary Intakes of Fish, Fat, and Fatty Acids", Kuriki et al, Last accessed Jul. 9, 2013, pp. 1-4.*
Ikai, Kouichi, Psoriasis and the arachidonic acid cascade, 1999, Journal of Dermatological Science, 21, pp. 135-146.*
Calvert, J. B., Peroxides, 2008, University of Denver, pp. 1-3.*
"Material Safety Data Sheet, B-Cap 35 Antimicrobial Agent", FMC Corporation, Nov. 11, 2009, pp. 1-11.
"Safety Data Sheet, Hydrogen Peroxide, 10% (w/w)", Columbus Chemical Industries, Inc., Dec. 3, 2012, pp. 1-6, <http://www.columbuschemical.com/MSDS/883600.pdf>.
"Material Safety Data Sheet, Hydrogen Peroxide 3% USP", U.S. Department of Labor, Apr. 10, 2007, pp. 1-4, <http://www.hydroxlabs.com/MSDS-23_Hydrogren_Peroxide_3%20_41007.pdf>.
"Hydrogen Peroxide", National Library of Medicine HSDB Database, Toxnet Toxicology Data Network, accessed May 27, 2015, pp. 1-42, <http://toxnetnlm.nih.gov/cgi-bin/sis/search/a?dbs+hsdb:@term+@DOCNO+547>.
"Hazardous Substance Fact Sheet, Hydrogen Peroxide", New Jersey Department of Health, Feb. 2008, pp. 1-6, <http://nj.gov/health/eoh/rtkweb/documents/fs/1015.pdf>.
"Hydrogen Peroxide Ingestions", ToxTidbits, Maryland Poison Center—University of Maryland School of Pharmacy, Mar. 2014, p. 1, <http://www.mdpoison.com/media/SOP/mdpoisoncom/ToxTidbits/2014/March2014ToxTidbits.pdf>.
"Clorox Healthcare Introduces New Line of Activated Hydrogen Peroxide Cleaner Disinfectants", The Clorox Company, Jan. 30, 2012, pp. 1-2, <https://www.cloroxprofessional.com/assets/News-room/Clorox-Healthcare-Introduces-Hydrogen-Peroxide.pdf>.

\* cited by examiner

*Primary Examiner* — Trevor Love
(74) *Attorney, Agent, or Firm* — Gregory N. Clements; Clements Bernard, PLLC

(57) ABSTRACT

The present invention relates to a stable, aqueous freshener composition for the reduction or elimination of malodors in air and on fabrics. The composition comprises from about 0.1% to about 3.0% by weight, hydrogen peroxide as a malodor oxidant; an effective level of undecylenic acid (and/or derivative thereof) as a malodor absorber preblended with a fragrance; a surfactant to solubilize the fragrance/malodor absorber blend; an acid based stabilizer in a range from about 0.008% to about 0.60% by weight; an optional pH buffer; and an aqueous carrier. The composition can be delivered via a spray dispenser for treatment of indoor air and fabrics. The composition has a pH of less than about 6 and does not contain ingredients known to soil, stain or damage fabrics. When applied as a fine mist, the composition delivers effective control of a broad range of malodors, while remaining imperceptible on surfaces when dry.

12 Claims, No Drawings

AIR AND FABRIC FRESHENER

FIELD OF THE INVENTION

The present invention relates to a stable, aqueous composition employed for odor control through reduction or elimination of malodors present in air and fabrics, such as carpet, clothing, upholstery, and drapery. The invention is directed to the use of hydrogen peroxide as a chemical oxidant in combination with existing odor control compositions including fragrance and non-fragrance deodorizing compounds. The composition is preferably delivered via a fine mist from a spray actuator into air and onto fabric surfaces to remove and reduce malodors. More than one odor control mechanism is employed in the composition including the chemical reaction (oxidation) of certain malodor molecules by hydrogen peroxide, thereby eliminating said molecules. Existing odor control compositions typically use fragrance and non-fragrance components to mask or otherwise interfere with the perception of malodors to the human olfactory system. The combination of hydrogen peroxide with these odor reduction components results in enhanced efficacy due to the action of the peroxide in breaking down the actual malodor molecule.

BACKGROUND OF THE RELATED ART

Air fresheners are products used in homes or commercial spaces to impart a pleasant smell. Some air freshener products simply deliver a fragrance; but most modern versions are designed to control malodors that may be present from food, tobacco, pets, the human body and other sources. The simplest approach to controlling malodors is fragrance masking, which is intentionally covering objectionable odors with a stronger fragrance or perfume scent. This approach typically requires a high level of fragrance to overcome the malodors, which may be irritating to breathing passages. Also, the scent of the fragrance used to mask odors may be objectionable as scent preferences can vary widely. Additionally, the malodor components are still present and may still be perceptible once the fragrance odor has dissipated.

Another approach to odor control is incorporation of an ingredient which absorbs, adsorbs, encapsulates, entraps or otherwise complexes with malodor molecules to reduce volatility or otherwise interfere with the perception of the malodor. This is referred to as odor neutralization in many cases. This mechanism does not involve a chemical breakdown of the malodor molecules by the odor control ingredient.

U.S. Pat. No. 3,102,101 assigned to Proctor & Gamble Co. discloses a sprayable composition to deodorize air comprising a hydrocarbon containing 12 to 18 carbon atoms, a propellant/carrier, and optionally a minor amount of pine oil. The proposed theory of why this composition works is called odor cancellation. As stated in the specification, odor cancellation does not encompass chemical interaction, and the components containing the C12 to C18 hydrocarbons are "extremely non-reactive". Since oxidizing components are reactive, these types of components are specifically excluded.

U.S. Pat. No. 6,495,097 assigned to Shaw Mudge & Co. discloses a composition for neutralizing odor comprising undecylenic acid (and/or derivatives thereof) and a fragrance. Further, undecylenic acid and/or derivatives thereof must be premixed with the fragrance at defined ratios and then introduced into a carrier or product which provides fragrance compositions that enhance neutralization of malodors while avoiding undesirable scavenging of fragrance. Undecylenic acid and derivatives thereof are neutralizing agents against malodor. This reference is hereby incorporated by reference as if its disclosure were set forth herein.

A chemical approach to odor control involves application of a reactive substance that eliminates the malodor molecule by changing it into a different molecule or molecules which are not malodors. This last approach is generally accomplished by oxidizing the malodor. An example is the oxidation of hydrogen sulfide (rotten egg odor) to elemental sulfur or sulfate ion. While this can be accomplished employing compounds such as sulfur dioxide, chlorine, ozone, or hydrogen peroxide; there are many problems with this approach. In large concentrations these oxidizing substances can corrode metal, damage other surfaces and are often harmful to people, especially to the lungs and breathing passages, including the nose. Fragrances are also very susceptible to oxidation such that these oxidizing substances can quickly neutralize fragrances. Lastly some of the oxidizing substances have odors of their own that may be unpleasant such as sulfur dioxide or chlorine.

U.S. Patent Application Publication 2006/0280665 assigned to S.C. Johnson & Son, Inc. discloses a vapor phase hydrogen peroxide deodorizer in which the composition is directed to passive evaporation of the hydrogen peroxide into the indoor air space. This invention excludes processes whereby aqueous compositions are dispersed into indoor space, or applied as a bulk liquid, or spraying liquid droplets such as by spraying, misting, fogging or atomizing. Since the desire here is to create a vapor phase deodorizer, neutralization may require 300 minutes or more. It is not quick neutralization like the present invention.

Hydrogen peroxide is an oxidizing and bleaching agent, meaning it will oxidize and destroy certain compounds. Typically the scents used in most cleaners fall into this group whereby they are destroyed. It would be difficult to find a scent that would stay stable in an aqueous peroxide solution. There are many that either degrade through oxidation by peroxide or induce instability in the peroxide itself. As stated in the *Handbook of Detergents*, Part D—Formulations, "Formulating a fragrance compatible with hydrogen peroxide is a difficult task since several common perfume ingredients, for instance aldehydes, can be unstable."

U.S. Pat. No. 4,238,192 assigned to S.C. Johnson & Son, Inc. discloses the neutralizing "composition can also include other standard ingredients which do not adversely affect the stability of the bleach. Perfumes can be incorporated. However, care must be exercised in the solution containing a perfume as these compositions are mixtures of many compounds, some of which may be susceptible to degradation by the hydrogen peroxide. Generally less than 1% perfume is used".

U.S. Pat. No. 5,942,153 assigned to Bush Boake Allen, Inc. discloses "A problem in the field of odor modification is in the area of perfuming bleaching compositions. Because of the inherent ability of a bleaching agent to destroy odors, it is difficult to effectively perfume a bleaching composition so that the perfume remains stable during storage and is available for effective delivery without being altered or destroyed by the bleach".

U.S. Patent Application Publication 2009/0226389 discloses in Table 1 fragrances that are stable with hydrogen peroxide for a short period of time. The perfumes/fragrances are only needed to mask the ammonia smell in a hair coloring composition. The 2 components are mixed together just before use. It is only necessary that the perfume be stable for a few minutes because there is no need for a long shelf life, as needed for the present invention. Note that the list in Table 1 is not complete, nor accurate for the present invention, since the present invention also contains undecylenic acid or a derivative thereof. Therefore the perfume must also be compatible with undecylenic acid or a derivative thereof. The present invention does not contain ammonia and none of the perfumes mentioned is stated to have a long shelf life. None of the ingredients in Table 1 is suitable for the present invention. Hair coloring compositions are not compatible with air and fabric fresheners.

Aerosol sprays are well known and are available in the market place using a compressed gas propellant along with the liquid composition in a sealed metal container or a manual pump sprayer with the liquid composition in a plastic or metal container. For the propellant sealed containers, depressing the nozzle creates a mist of aerosol liquid droplets which can be applied to fabric or to room air to neutralize bad odors. For manual pump sprayers, the container is re-fillable and upon squeezing the trigger of the sprayer, a mist of aerosol liquid droplets can be applied to fabric or to room air to neutralize bad odors.

SUMMARY OF THE INVENTION

The present invention relates to water-based air and fabric freshener compositions which may be used to control odor through the controlled release of a perfume long-lasting pleasant scent combined with a dual mechanism approach to reducing and eliminating malodors or the perception thereof. Non-reactive odor neutralizing agents adsorb, absorb, entrap, encapsulate or complex with malodors to render them less volatile or otherwise unavailable for perception to the human olfactory system. Hydrogen peroxide reacts with certain malodor molecules eliminating them through oxidative destruction. The combination of these mechanisms can treat a broad range of malodors. Compositions are applied by spraying or misting into air or onto fabric surfaces where the aqueous phase, in finely dispersed droplets, facilitates intimate contact with and interaction between malodor molecules and odor counteractants. Malodors are then eliminated from the air or fabric following treatment with these compositions.

In the broadest sense, the present invention is a freshener composition for air and fabric, comprising (A) hydrogen peroxide in a range from about 0.1 to about 3.0 wt. %; (B) a non-reactive malodor neutralizer; (C) fragrance or perfume; (D) a surfactant in an amount sufficient to solubilize fragrance and any other water-insoluble components; (E) a stabilizer for hydrogen peroxide; (F) an aqueous carrier wherein water is present at a quantity sufficient for formulation to total 100 wt. %. Optionally, various additives may be employed such as a buffer system, additional fragrances, solvents, antimicrobial agents, or preservatives.

DETAILED DESCRIPTION OF THE PREFERRED EMBODIMENTS

The ranges set forth herein include not only those numbers defining the beginning and the end point of the range, but also every conceivable number in between, as that is the very definition of a range. Furthermore, when the word "about" is used before a number, it is meant to cover numbers slightly outside the specified range, but not intended to eliminate a component, or make it optional, unless the range specifically specifies zero.

The present invention relates to a freshener composition for air and fabric, comprising: (A) hydrogen peroxide in a range from about 0.1 to about 3.0 wt. %; (B) a premix of fragrance and undecylenic acid (and/or derivative thereof) in a range from about 0.5 to about 2.5% wt. %; (C) a surfactant in a range of about 0.1 to about 12.5 wt. %; (D) an acid based stabilizer in a range of about 0.008 to 0.60 wt. %; and (E) an aqueous carrier. The composition may also contain (F) a buffer system to control pH fluctuation over the shelf life of the product and (G) optional standard ingredients which do not adversely affect the performance or stability of the composition.

(A) Hydrogen Peroxide

The air and fabric freshener composition of the present invention employs hydrogen peroxide in an amount or range from about 0.1 to about 3.0 wt. %, based on the total weight of the freshener composition. Hydrogen peroxide is sold commercially in aqueous solution. The present invention uses hydrogen peroxide commercially available under the name of Super D 35% from FMC Corporation. Other similar peroxide commercially available products are also available. Super D is 35% aqueous hydrogen peroxide. The amount of Super D 35% aqueous solution of hydrogen peroxide would be employed in a range of about 0.3 to about 9 wt. %, yielding about 0.1 to about 3.0 wt. % of active hydrogen peroxide. At the specified range of hydrogen peroxide, the freshener compositions are safe for use in indoor environments around humans and pets and will not corrode metal or fade or damage fabrics.

(B) Fragrance/Odor Neutralizer

A pre-mix of undecylenic acid (or a derivative thereof) and a fragrance are typically employed in the range of 0.5 to 2.5 wt. % of the freshener composition of the present invention. As set forth in U.S. Pat. No. 6,495,097, the pre-mix contains fragrance in a range of 50-95 wt % and undecylenic acid or its derivatives in a range of 5-50 wt. %, both based on the total weight of the pre-mix. Derivatives of undecylenic acid are salts of the acid—such as sodium, calcium or zinc, simple esters such as its methyl, ethyl, propyl, and butyl ester forms, or undecylenate silicone esters, or a mixture of these salts or these esters. The term fragrance as used in consumer products typically refers to a mixture of many individual chemical components custom blended to deliver a particular scent. Fragrance components may be extracted from natural aromatic sources such as flowers (e.g., lavender, lilac, rose, jasmine, gardenia), trees (e.g., pine or vanilla scents), or food such as melon or berries. Formulated fragrances may be synthetic, natural or mixtures of synthetic and natural components. These components makeup an enormous class of chemicals and the possible combinations of these components are almost limitless. It requires rigorous testing to determine if a fragrance is pleasant and acceptable to a large portion of the population. For the present invention, the fragrance must be shelf stable, compatible with hydrogen peroxide, and compatible with undecylenic acid and/or its derivatives. For the present invention "stable and compatible" means that the freshener must have a shelf stability of at least one year. Because hydrogen peroxide neutralizes many fragrances, very few are stable and compatible with the present invention. Additional odor neutralization ingredients and fragrances may be employed in place of the compositions disclosed in U.S. Pat. No. 6,495,097 provided they are stable and compatible with hydrogen peroxide and other ingredients of the composition.

(C) Surfactant

A surfactant is a compound that lowers the surface tension of water, thereby imparting associated functional properties when incorporated into an aqueous solution including wetting/spreading of product upon application and solubilization of non-water soluble components such as a fragrance in an aqueous carrier. The preferred surfactant in the freshener composition of the present invention is PEG-20 sorbitan laurate; commonly known as polysorbate 20; commercially supplied under trade name Tween® 20 by Croda. Alternate trade name sources of polysorbate 20 are also available. Moreover many other types of surfactants may be suitable provided they are functional as solubilizers and wetting agents and stable with hydrogen peroxide and other freshener components of the present invention. Suitable surfactants which are typically used as solubilizers include but are not limited to other ethoxylated sorbitan esters, ethoxylated castor oil derivatives, polyhydric alcohols such as propylene glycol, propanediol, dipropylene glycol, polyglyceryl esters, and glycol/propylene glycol block copolymers commonly known as poloxamers. The polysorbate 20 is used in a range of about 2.5 to 7.5 wt. %, based on the weight of the total freshener composition. The usage range for other suitable surfactants would depend upon the nature of the surfactant and the amount and composition of water-insoluble components to be solubilized. Surfactant class is not limited to nonionic; but can be anionic, cationic, amphoteric or zwitterionic and mixtures thereof; provided they are compatible/stable with hydrogen peroxide and the other components. To cover all these surfactants, the range of 0.1 to 12.5 wt %, based on the wt. of the total freshener composition is suitable for the present invention. Preferably, surfactant or surfactant mixture forms low or no foam aqueous solutions. Optionally, a defoaming agent may be used in combination with solubilizing/wetting surfactants.

(D) Acid Based Stabilizer

The composition contains an acid based stabilizer which can include a mixture of more than one acid and/or salt. The function is to enhance the stability of the hydrogen peroxide in solution while maintaining its oxidation capacity upon application. Phosphorus based acids and salts thereof are preferred and may be inorganic or organic with phosphoric acid and phosphonates being most preferred. Phosphorus based acids and/or salts are employed in a range of 0.008 to 0.60 wt. % based on the weight of the freshener composition, which is sufficient for adequate stability and activity. Phosphoric acid, like the hydrogen peroxide is commercially available in aqueous solution. Phosphoric acid 85 wt. % (aqueous solution) is used in the present invention. The range of the 85% aqueous solution is about 0.01 to about 0.70 wt. %.

(E) Aqueous Carrier

The remainder of the composition is the aqueous carrier—water, preferably deionized water. The quantity of water is sufficient for the composition to total 100% wt. Additional optional ingredients would reduce the quantity of water by the total % wt. of such added ingredients so that the total composition is 100% wt.

(F) Optional Buffer

A buffer system to control fluctuating pH over the shelf life of a product may also be present. The preferred buffer includes citric acid and sodium citrate (the sodium salt of citric acid) in a range of about 1 part citric acid to 2-3 parts sodium citrate. The total amount of buffer system employed in the freshener composition is about 0.1 to about 0.4 wt. % based on the weight of the composition and provides a pH of 5.0±1.0. Other buffer systems compatible with all the components of the composition, and suitable for the invention include organic and inorganic acids and their salts where the ratio of acid to salt and the total amount of buffer system in the composition are determined by the type of acid and the desired pH.

(G) Other Optional Ingredients

Standard optional ingredients may be contained in the composition of the present invention provided they do not adversely affect the performance or stability of the composition. Examples of optional ingredients include adjunct fragrance and odor-control agents, stabilizing agents, solubilizing agents, odor-control agents, solvents (including alcohols), antimicrobials, antioxidants, colorants, antifoaming agents and mixtures thereof. The total of all optional ingredients can be up to about 6 wt. %, based on the weight of the freshener composition. Preferably the total of all optional ingredients is up to about 1 wt. %.

The preferred composition of the present invention comprises the following components: deionized water present in quantity sufficient to bring total composition to 100% wt.; 35 wt. % hydrogen peroxide aqueous solution in a range of 0.3 to 9.0 wt. % (wherein the actual amount of the hydrogen peroxide would be 35 wt. % of each of these two range limits—about 0.1 to about 3 wt %); Tween 20® surfactant in a range of about 2.5 to 7.5 wt. %; a pre-mix in a range of about 0.5 to 2.5 wt. % which comprises fragrance and undecylenic acid and/or its derivatives; 85 wt. % phosphoric acid aqueous solution in a range of about 0.01 to 0.7 wt. % (wherein the actual amount of the acid is in a range of about 0.008 to about 0.60 wt. % based on the weight of the freshener composition); citric acid anhydrous in a range of about 0.05 to 0.1 wt. %; sodium citrate dihydrate in a range of about 0.1 to 0.3 wt. %; wherein the range of these components comprise 100 wt. % of the freshener composition.

To make a composition of the present invention, the pre-mix is prepared by mixing fragrance in the range of about 50-95 wt. % with undecylenic acid and/or its derivative in a range of 5-50 wt. %, based on the total weight of the pre-mix. The premix is then thoroughly mixed with the surfactant solubilizer. Thereafter, premix and other components are merely blended together in a uniform consistency, using a plastic or stainless steel container/reactor. The composition may then be introduced into a plastic spray bottle with a manual hand pump such that it can be sprayed in air or on fabric to reduce or neutralize malodors.

EXAMPLES

The following are non-limiting examples of the present invention. Ingredient amounts disclosed are wt. % based on 100 wt. % of composition.

| Description/Chemical Name | Ex. 1 | Ex. 2 | Ex. 3 | Ex. 4 | Ex. 5 | Ex. 6 | Ex. 7 | Ex. 8 | Ex. 9 | Ex. 10 |
| --- | --- | --- | --- | --- | --- | --- | --- | --- | --- | --- |
| Deionized Water | to 100 | to 100 | to 100 | to 100 | to 100 | to 100 | to 100 | to 100 | to 100 | to 100 |
| Hydrogen Peroxide 35% | 0.30 | 0.30 | 0.30 | 0.30 | 0.30 | 0.30 | 0.30 | 0.30 | 0.30 | 0.30 |
| Preblend Classic Fresh Fragrance | 1.00 | 1.00 | 1.00 | 1.00 | 1.00 | 1.00 | 1.00 | | 1.00 | |
| Preblend Cool Springs Fragrance | | | | | | | | 1.00 | | 1.00 |
| Polysorbate 20 | 5.00 | 5.00 | 5.00 | 5.00 | 5.00 | 5.00 | 5.00 | 5.00 | 5.00 | 5.00 |
| Phosphoric Acid 85% | 0.04 | 0.07 | 0.04 | 0.04 | 0.04 | 0.04 | 0.04 | 0.05 | 0.04 | 0.04 |
| Sodium Hydroxide 10% | 0.17 | 0.20 | 0.18 | 0.18 | 0.18 | 0.18 | 0.18 | 0.20 | 0.14 | 0.12 |
| Isopropanol 91% | 5.00 | | | | | | | | | |
| Euxyl K 220 (proprietary preservative blend)₁ | 0.10 | | | | | | | | | |

-continued

| | | | | | | | | | | |
|---|---|---|---|---|---|---|---|---|---|---|
| Acticide MBS (proprietary preservative blend)[2] | | 0.20 | | 0.20 | 0.35 | 0.50 | | | | |
| Acticide MV (proprietary preservative blend)[3] | | | | | | | 0.10 | 0.10 | 0.10 | |
| % H2O2 | 0.11 | 0.11 | 0.11 | 0.11 | 0.11 | 0.11 | 0.11 | 0.11 | 0.11 | 0.11 |
| pH | 4.38 | 4.80 | 5.05 | 5.05 | 5.05 | 5.05 | 5.05 | 5.83 | 5.10 | 5.37 |

[1] Methylisothiazolinone (and) ethylhexylglycerin (Schulke)
[2] Methylchloroisothiazolinone (and) methylisothiazolinone (Thor)
[3] Benzisothiazolinone (and) methylisothiazolinone (Thor)

| Description/Chemical Name | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| Deionized Water | to 100 | to 100 | to 100 | to 100 | to 100 | to 100 | to 100 | to 100 | to 100 | to 100 |
| Hydrogen Peroxide 35% | 0.30 | 1.43 | 1.43 | 2.86 | 2.86 | 0.30 | 0.30 | 1.43 | 1.43 | 0.30 |
| Preblend Classic Fresh Fragrance | 1.00 | | 1.00 | | 1.00 | | 1.00 | | 1.00 | |
| Preblend Cool Springs Fragrance | | 1.00 | | 1.00 | | 1.00 | | 1.00 | | 1.00 |
| Polysorbate 20 | 5.00 | 5.00 | 5.00 | 5.00 | 5.00 | 5.00 | 5.00 | 5.00 | 5.00 | 5.00 |
| Phosphoric Acid 85% | 0.05 | 0.09 | 0.04 | 0.04 | 0.05 | 0.02 | 0.02 | 0.02 | 0.02 | 0.02 |
| Sodium Hydroxide 10% | 0.15 | 0.25 | 0.15 | 0.13 | 0.25 | | | | | |
| Isopropanol 91% | | | | | | | | | | |
| Acticide MV (proprietary preservative blend)[1] | | | | | | 0.10 | 0.10 | | | |
| Citric Acid | | | | | | 0.07 | 0.07 | 0.07 | 0.07 | 0.07 |
| Sodium Citrate | | | | | | 0.19 | 0.19 | 0.27 | 0.19 | 0.19 |
| % H2O2 | 0.11 | 0.48 | 0.49 | 0.99 | 1.00 | 0.11 | 0.11 | 0.49 | 0.49 | 0.10 |
| pH | 5.06 | 5.54 | 5.12 | 5.50 | 5.56 | 4.90 | 5.03 | 5.13 | 4.95 | 4.90 |

[1] Benzisothiazolinone (and) methylisothiazolinone (Thor)

| Description/Chemical Name | Ex. 21 | Ex. 22 | Ex. 23 | Ex. 24 |
|---|---|---|---|---|
| Deionized Water | to 100 | to 100 | to 100 | to 100 |
| Hydrogen Peroxide 35% | 0.30 | 2.86 | 2.86 | 0.30 |
| Preblend Classic Fresh Fragrance | 1.00 | | 1.00 | |
| Preblend Cool Springs Fragrance | | 1.00 | | |
| Preblend Cool Springs/Lavender Fragrance | | | | 1.00 |
| Polysorbate 20 | 5.00 | 5.00 | 5.00 | 5.00 |
| Phosphoric Acid 85% | 0.02 | 0.02 | 0.02 | 0.02 |
| Citric Acid | 0.07 | 0.07 | 0.07 | 0.07 |
| Sodium Citrate | 0.19 | 0.19 | 0.19 | 0.19 |
| % H2O2 | 0.10 | 1.01 | 1.04 | 0.10 |
| pH | 4.85 | 5.04 | 5.23 | 4.83 |

Polysorbate 20 and Preblend fragrances were premixed and then all ingredients were combined and mixed until clear and uniform.

Odor Testing

An odor panel test was conducted to evaluate the malodor reduction/elimination efficacy on a comparison basis of Examples 8, 9 and a commercially available fabric refresher as sold under the name Febreze® extra Strength as sold by the Proctor and Gamble Company.

The test substrate was clean, cotton/polyester cloth, cut into 3"×4" swatches for evaluation with malodors.

A group of swatches were impregnated with cigarette smoke in a "smoke box", allowing the odor to penetrate overnight. A second group of swatches were impregnated with cat urine collected from a local veterinarian. A third group of swatches were impregnated with a food solution made from chopped onions, minced garlic, bacon grease and beef fat, in roughly equal proportions, heated on a hot plate until the onions browned.

The swatches were allowed to dry overnight and then treated with 2.0±0.2 grams of test product. Designated swatches of each odor group were left untreated as a control for reference in the panel evaluations.

The swatches were arranged in pairs so that for each malodor, swatches treated with one test product were paired in triplicate with swatches treated with the other sample and a blank "control". The panel then judged the pairs.

Each panel member was given an untreated swatch to smell as a target—the swatch contained the odor, but not any air freshener. Then they were presented with the swatches, one set at a time, and asked to pick the member of each pair that has reduced the target odor the best. Each malodor group of swatches was evaluated independently.

The data from all the panel members were tabulated and analyzed per the Friedman Analysis described in *Sensory Evaluation Techniques* by Meilgaard, Civille and Carr. The result is a score for each product and the difference between the scores that is statistically significant. Higher scores are better and show less of a resemblance to the target odor.

Results:

| | Odor Reduction Scores | | |
|---|---|---|---|
| Sample | Cat Urine | Food | Cigarette |
| Example 8 | 112 | 113 | 127 |
| Febreze, Extra Strength | 105 | 105 | 104 |
| Example 9 | 107 | 106 | 93 |
| Sig. Dif. | 17 | 17 | 17 |

Example 8 performed the best in all odor reduction. The Febreze sample and Example 9 are comparable in odor reduction on cat urine and food odor.

Stability Testing

Examples 1, 2, and 8-24 were predicted to be shelf stable for at least one year based on passing test results after storage at elevated temperature (45C) for at least 8 weeks. Samples were evaluated for 12 weeks. Examples 1, 2, 8 and 9 were evaluated for appearance, scent and pH. Examples 10-24 were evaluated for appearance, scent, pH and % hydrogen peroxide.

Stability samples were monitored by testing every 2 weeks. Appearance and scent evaluations were subjective, a Hanna HI 2211 pH/ORP Meter was used for pH measurements and an iodometric titration method was used to determine % hydrogen peroxide.

Examples were determined to be stable based on above method provided test parameter changes were not significant after 8 weeks at elevated temperature as compared to initial values.

A minor pH drift was noted in stability testing of Examples 2 and 8-15 where final pH (8 weeks at 45C) was lower than initial value by more than one unit. Example 1 which contained isopropanol at 5 wt. %, was stable with respect to pH. A buffer system was incorporated into Examples 16-24 which resulted in pH change of <0.2 units.

Preservative Efficacy Testing

Examples 3-7 were prepared with varying levels of preservative additives for preservative efficacy testing.

Example 3 was prepared as the control sample with no traditional preservative additive and only the hydrogen peroxide at 0.1 wt. % for protection against antimicrobial contamination.

Wet state bacterial (A720, A721 Methods$_1$) and fungal (A730, A731 Methods$_1$) challenge testing was conducted on examples 3-7 using the following microorganisms.

(1) Test methods—Thor Specialties, Inc.

| Thor Standard Wet State Resistance Test Inocula | |
|---|---|
| Organism | Culture Collection Reference |
| For Test Methods A720 and A750 Bacterial cultures | |
| *Aeromonas hydrophilia* | ATCC 35654 |
| *Alcaligenes faecalis* | ATCC 8748 |
| *Corynebacterium ammoniagenes* | ATCC 6871 |
| *Enterobacter aerogenes* | ATCC 13048 |
| *Escherichia coli* | ATCC 8739 |
| *Klebsiella pneumoniae* | ATCC 9621 |
| *Proteus hauseri* | ATCC 13315 |
| *Providencia rettgeri* | ATCC 29944 |
| *Pseudomonas aeruginosa* | ATCC 9027 |
| *Serratia liquefaciens* | ATCC 27592 |
| *Shewanella putrefaciens* | ATCC 49138 |
| For Test Methods A730 and A750 Mold cultures | |
| *Aspergillus oryzae* | ATCC 11488 |
| *Cladosporium species* | ATCC 28310 |
| *Geotrichum candidum* | ATCC 34380 |
| *Paecilomyces variotti* | ATCC 24330 |
| *Penicillium ochrochloron* | ATCC 9112 |
| *Sporothrix species* | ATCC 66734 |
| For Test Methods A730, A740, and A750 Yeast cultures | |
| *Candida albicans* | ATCC 10231 |
| *Candida guillermondi* | ATCC 20216 |
| *Candida valida* | ATCC 22687 |
| *Rhodotorula glutinis* | ATCC 32765 |

Wet State Bacterial Resistance Test—Nutrient Agar Inoculum was as follows.

1$^{st}$ inoculation: 2.0×10$^6$ cfu/ml
2$^{nd}$ inoculation: 2.0×10$^6$ cfu/ml
3$^{rd}$ inoculation: 1.0×10$^6$ cfu/ml Samples were inoculated three times and evaluated for growth 2 and 5 days after each inoculation. A 12 day growth evaluation was also done after 3$^{rd}$ inoculation.

Wet-state bacterial challenge testing results showed no growth at any test point, in any of the test samples including the unpreserved (hydrogen peroxide only) fabric spray base sample.

Wet State Fungal Resistance Test—PDA (Potato Dextrose Agar Streak Plates) Inoculum as follows.

Yeast: 2.2×10$^7$ cfu/ml

Mold: 4.4×10$^5$ cfu/ml

Samples were incubated at 25C for 3 weeks and evaluated for growth.

Wet-state fungal challenge testing results showed no growth in any of the test samples including the unpreserved (hydrogen peroxide only) fabric spray base sample.

It was unexpectedly discovered that the unpreserved (hydrogen peroxide only) control sample (Example 3) was determined to be adequately preserved without additional antimicrobial ingredients with the low active hydrogen peroxide level of 0.1 wt. %.

Thus it apparent that there has been provided in accordance with the invention, a freshener for air and fabric that fully satisfies the objects, aims, and advantages set forth above. While the invention has been described in conjunction with specific embodiments thereof, it is evident that many alternatives, modifications, and variations will be apparent to those skilled in the art in a lot of the foregoing description. Accordingly, it is intended to embrace all such alternatives, modifications and variations that fall within the spirit and broad scope of the appended claims.

What is claimed is:

1. A freshener composition for air and fabric, comprising: hydrogen peroxide in a range from about 0.1 to about 3.0 wt. %; a premix of fragrance and ethyl or methyl undecylenate in a range from about 0.5 to about 2.5% wt. %; a surfactant in a % wt. range from about 0.1 to about 7.5 wt.; an acid based stabilizer in a range of about 0.008 to 0.0765 wt. %; and a quantity of water sufficient to bring total to 100 wt. % wherein said fragrance is compatible with said hydrogen peroxide.

2. The composition of claim 1, wherein said surfactant is nonionic.

3. The composition of claim 2, wherein said nonionic surfactant is an ethoxylated sorbitan ester.

4. The composition of claim 3, wherein said ethoxylated sorbitan ester is polysorbate 20 (PEG-20 Sorbitan Laurate).

5. The composition of claim 1, wherein said acid based stabilizer is a phosphorus based acid or salt.

6. The composition of claim 5, wherein said phosphorus based acid is phosphoric acid and phosphonates.

7. The composition of claim 1, wherein said water is deionized water.

8. The composition of claim 1, further comprising a pH buffer system.

9. The composition of claim 8, wherein said pH buffer system is citric and sodium citrate.

10. The composition of claim 9, wherein said citric acid and sodium citrate is in a range of about 1 part citric acid to 2-3 parts sodium citrate.

11. The composition of claim 8, wherein the total amount of buffer system employed in the freshener composition is between about 0.2 to 0.4 wt. % based on the weight of the composition.

12. The composition of claim 1, wherein said composition has a shelf stability of at least one year.

* * * * *